United States Patent [19]

Horvath et al.

[11] 4,168,001
[45] Sep. 18, 1979

[54] SUTURE AND NEEDLE HOLDER

[76] Inventors: Ralph S. Horvath, Rte. 1, Box 244B, Houghton, Mich. 49931; Annette M. Chapel, Massie Rd., Chassell, Mich. 49916

[21] Appl. No.: 873,454

[22] Filed: Jan. 30, 1978

Related U.S. Application Data

[62] Division of Ser. No. 715,726, Sep. 19, 1976, Pat. No. 4,105,115.

[51] Int. Cl.² ............................................. A61L 17/02
[52] U.S. Cl. ................................. 206/370; 206/63.3; 206/382; 206/459; 206/460; 206/620
[58] Field of Search ................... 223/107, 108, 109 R; 206/380, 382, 0.84, 63.3, 459, 460, 602, 370, 438, 820, 620; 248/205 A

[56] References Cited

U.S. PATENT DOCUMENTS

| | | | |
|---|---|---|---|
| 2,119,773 | 6/1938 | Buckner | 206/0.84 |
| 2,372,994 | 4/1945 | Welch | 206/820 X |
| 2,653,703 | 9/1953 | Krauss | 206/0.84 |
| 2,705,203 | 3/1955 | Heidrich et al. | 206/820 X |
| 2,954,120 | 9/1960 | Norcross | 206/0.84 |
| 3,021,001 | 2/1962 | Donofrio | 206/602 |
| 3,080,963 | 3/1963 | Rothgart | 206/0.84 |
| 3,138,244 | 6/1964 | White | 206/0.84 X |
| 3,191,791 | 6/1965 | Jackson | 217/25.5 |
| 3,329,277 | 7/1967 | Gaudino | 206/0.84 X |
| 3,338,395 | 8/1967 | Silverstein | 206/459 X |
| 3,476,257 | 11/1969 | O'Connell | 248/205 A X |
| 3,481,462 | 12/1969 | Chapel | 206/438 |
| 3,579,878 | 5/1971 | Griffin et al. | 206/0.84 X |
| 3,696,920 | 10/1972 | Lahay | 206/370 |
| 3,712,465 | 1/1973 | Deuschle | 206/459 |
| 3,819,039 | 6/1974 | Erickson | 24/205 A X |
| 3,944,069 | 3/1976 | Eddridge, Jr. | 206/460 X |
| 3,983,999 | 10/1976 | Morton | 206/602 |
| 4,008,802 | 2/1977 | Freitag | 206/63.3 |

*Primary Examiner*—Allan N. Shoap
*Attorney, Agent, or Firm*—Cullen, Sloman, Cantor, Grauer, Scott & Rutherford

[57] ABSTRACT

A holder for retaining sutures, needles and other surgical products used during surgical operations, with one form of the holder being made from sheet material and having intermediate portions folded over adjacent intermediate portions thereof to form a plurality of pockets which are adapted to receive and retain the sutures and needles. Such holder is provided with one or more detachable blocks of resilient material having indicia thereon for assisting in counting the needles carried by the blocks. The holder may be provided with a foldable easel stand. Another embodiment consists of a block of polyfoam material divided into first and second sections, with the first section having on the top wall thereof a decal with indicia thereon and with the second section having in the top wall thereof parallel slots for receiving surgical sutures, needles, etc. to hold them securely and conveniently in place. After the sutures and needles have been accounted for by indicating same on the decal, the first and second sections of the block are severed, with the second section containing the used sutures and needles being disposed of and with the first section being retained.

4 Claims, 17 Drawing Figures

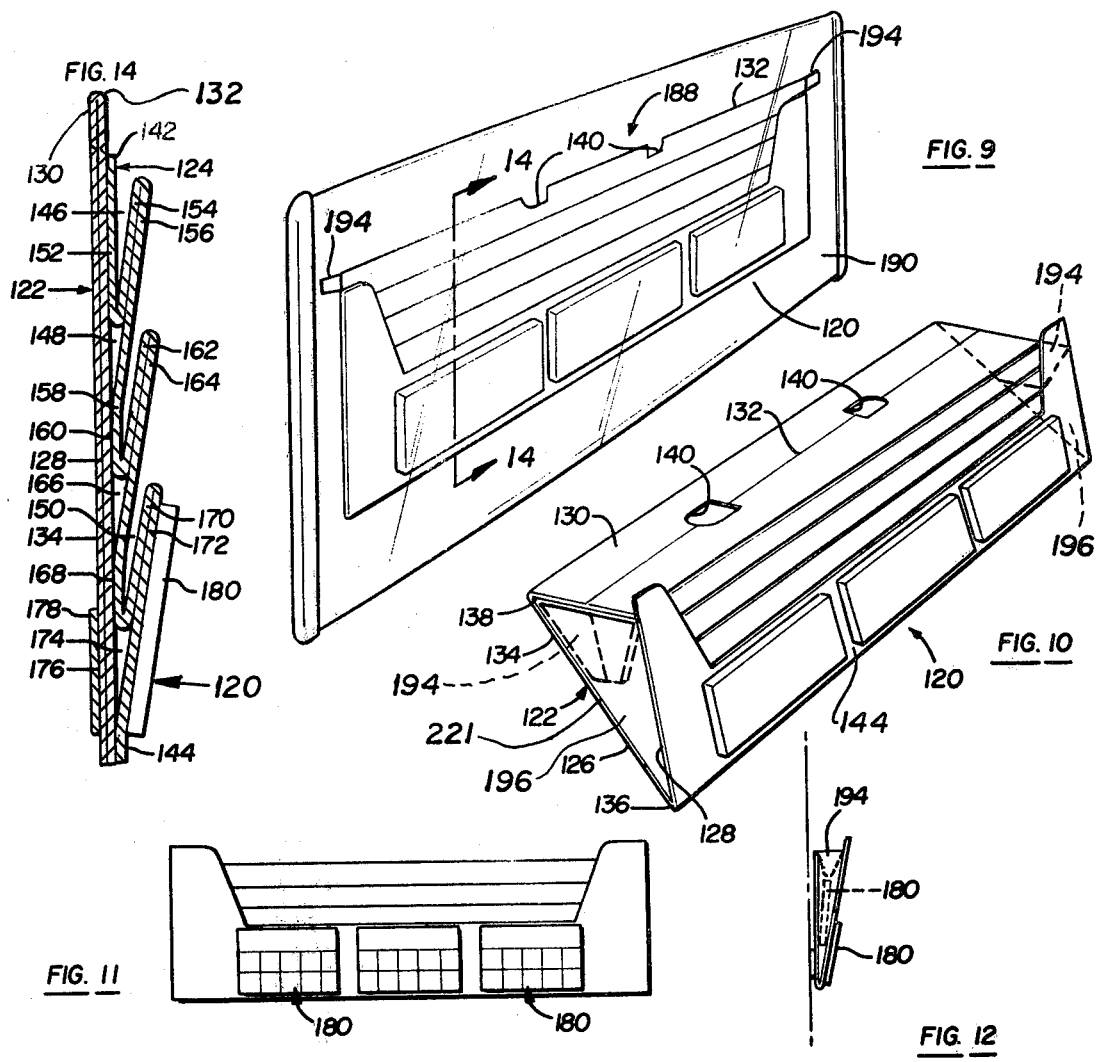
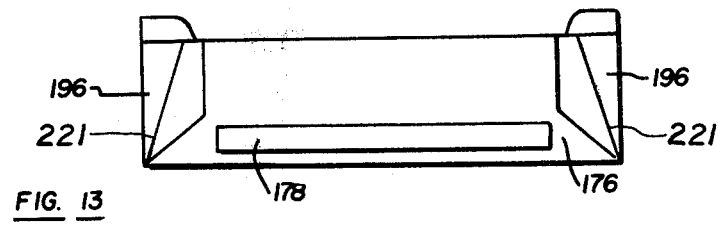
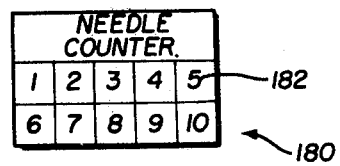
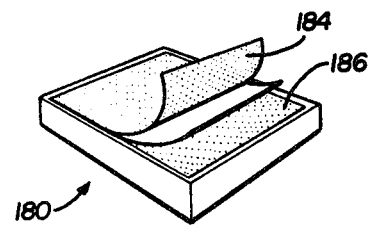

SUTURE AND NEEDLE HOLDER

This is a division of application Ser. No. 715,726, filed Aug. 19, 1976, now U.S. Pat. No. 4,105,115 issued Aug. 8, 1978.

BACKGROUND OF THE INVENTION

1. Field of the Invention

The surgical holder or holder and counter is used by doctors and nurses in operating rooms and hospitals when it is required to account for sutures, needles and other surgical products and items used during operations.

This invention relates to surgical accessories and more specifically to a holder for retaining sutures, needles and other surgical products.

2. Description of the Prior Art

During surgical operations, a scrub technician or operating room assistant is required to supply the surgeon with sutures as the occasion arises. The common procedure of holding sutures in place is to arrange bundles of sutures within the folds or pleats of ordinary towels. An average size towel has a limited capacity for holding the sutures. As the bundles become larger, they become correspondingly unmanageable and individual sutures become entangled and stuck together. Also, the individual sutures are not held stably within the folds so when the scrub technician attempts to remove one suture from a bundle it is not uncommon for two or more sutures to become released which slows down the procedure.

In order to keep the towel stationary as it holds the sutures, medical instruments are used to weigh it down. If the table upon which the towel rests is jolted then the folds may become opened and the sutures permitted to fall onto the floor. The cumbersome and annoying drawbacks of these foregoing conventional procedures have resulted in certain inventions which have attempted to improve on the present practices but such inventions have not been successfully commercialized.

It is also the standard practice in an operating room for the responsible nurse or person to actually count all sponges, needles and other surgical products used during or made available for the opration to insure that such products have not been left within the interior or a cavity of the patient's body upon completion of the operation. Since the nurse has many other duties in the operating room, it is difficult for the nurse to remember the exact count and to physically keep track of the surgical products utilized.

A search located the following patents which attempt to solve certain of the foregoing problems including the prior patents to Chapel, U.S. Pat. No. 3,481,462 of Dec. 2, 1969 and the patents cited therein; Erickson, U.S. Pat. No. 3,819,039 of June 25, 1974; Slomczewski, U.S. Pat. No. 3,388,790 of June 18, 1968; Grover, U.S. Pat. No. 2,692,676 of Oct. 26, 1954; Tauber U.S. Pat. No. 2,588,589 of Mar. 11, 1952; Dean, U.S. Pat. No. 2,583,043 of Jan. 22, 1952; and Choffel, U.S. Pat. No. 2,176,452 of Oct. 17, 1939.

SUMMARY OF THE INVENTION

It is therefore a feature of the present invention to provide a holder for sutures, needles and other surgical components or a holder and counter which is constructed and arranged to hold or support a plurality of sutures and associated needles in such a manner that a suture or sutures are readily available to the surgeon when operating.

A further feature of the present invention is to provide a suture-needle rack or holder which is constructed and arranged so that a plurality of sutures are held in distended separated relation with the needles associated therewith held in separated relation whereby a needle and suture may be easily and readily engaged by the surgeon when necessary.

It is a further feature of the present invention to provide a holder and counter that is simple in construction, economical to manufacture, convenient to use and efficient to operate, and able to meet operating room sterility requirements.

It is a still further feature of the present invention to provide a suture-needle holder and counter that is easy to load and set up for use and from which sutures and needles can be identified and removed singly or in groups without mishaps in an operating room.

Another feature of the present invention is to provide a light-weight, inexpensive, relatively handy suture-needle rack or holder for conveniently and positively holding numerous individual surgical sutures and needles so that a selected suture or suture and needle may be rapidly withdrawn from the holder without disturbing or otherwise adversely affecting the other surgical products.

Still another feature of the present invention is to provide a suture-needle rack or holder of the aforementioned type wherein removable blocks with indicia are secure to an area of the holder to permit the nurse to insert and count the needles before, during and after use and conveniently remove the same from the sterile operating area.

Still another feature of the present invention is to provide a holder of the aforementioned type wherein a foldable easel or stand is provided for mounting the holder on a support. With such a construction, the stand also provides a pocket or opening into which the contaminated needles may be safely placed. Thereafter, the ends of the stand or holder are folded over and the entire pocket is discarded with no ensuing danger to janitorial personnel.

A further feature of the present invention is to provide a holder for surgical products having portions thereof folded over adjacent portions thereof to form a plurality of pockets adapted to receive surgical products.

A still further feature of the present invention is to provide a holder for surgical products comprising an elongated base member, an elongated facing member secured to one side of the base member, with the facing member having a pair of longitudinal edge portions and a plurality of longitudinal intermediate portions between the edge portions, and with the intermediate portions being folded over adjacent portions thereof to define a plurality of longitudinally extending pockets adapted to receive surgical products.

Another feature is to provide a holder of the aforementioned type wherein the base member and the facing member are made from relatively thin poster board, with the facing member having the longitudinal edge portions thereof secured to the base member.

Still another feature is to provide a holder of the aforementioned type wherein a pressure-sensitive adhesive strip is secured to the other side of the base member for attaching the holder to a support.

A further feature is to provide a holder of the aforementioned type wherein a decal with indicia is secured to the facing member to permit a person to account thereon for the surgical products utilized.

A still further feature of the present invention is to provide a holder of the aforementioned type wherein the holder, after being sterilized is provided with an outer envelope which is sealed to maintain the holder in a sterilized condition.

Another feature of the present invention is to provide a holder and counter for surgical products comprising a generally rectangular elongated block having a flat top wall and a flat bottom wall, a groove extending through the top wall and terminating short of the bottom wall and dividing the block into two sections, a decal with indicia thereon secured to the top wall of one of the sections, the other section having a plurality of parallel and lengthwise extending slots passing entirely through the top wall and extending towards the bottom wall and which are adapted to receive surgical products, the first and second sections being severable after the products have been used by applying a force to the bottom wall adjacent the groove to separate the sections of the block.

BRIEF DESCRIPTION OF THE DRAWINGS

FIG. 9 is a perspective view of still another embodiment of the present invention sealed in a transparent envelope;

FIG. 10 is a perspective view of the holder and counter of FIG. 9 removed from the package, and with the foldable easel stand opened and ready to be mounted or placed on a support;

FIG. 11 is a front view of the holder and counter shown in FIG. 10;

FIG. 12 is a side view of the holder and counter shown in FIG. 10;

FIG. 13 is a back view of the holder and counter shown in FIG. 10;

FIG. 14 is a sectional view of the holder and counter taken on the line 14—14 of FIG. 9, with the package removed;

FIG. 15 is a front view of the needle block; and

FIG. 16 is a perspective view of the needle block provided with two pressure-sensitive adhesive strips.

DESCRIPTION OF PREFERRED EMBODIMENTS

Figures 1, 2, 3:
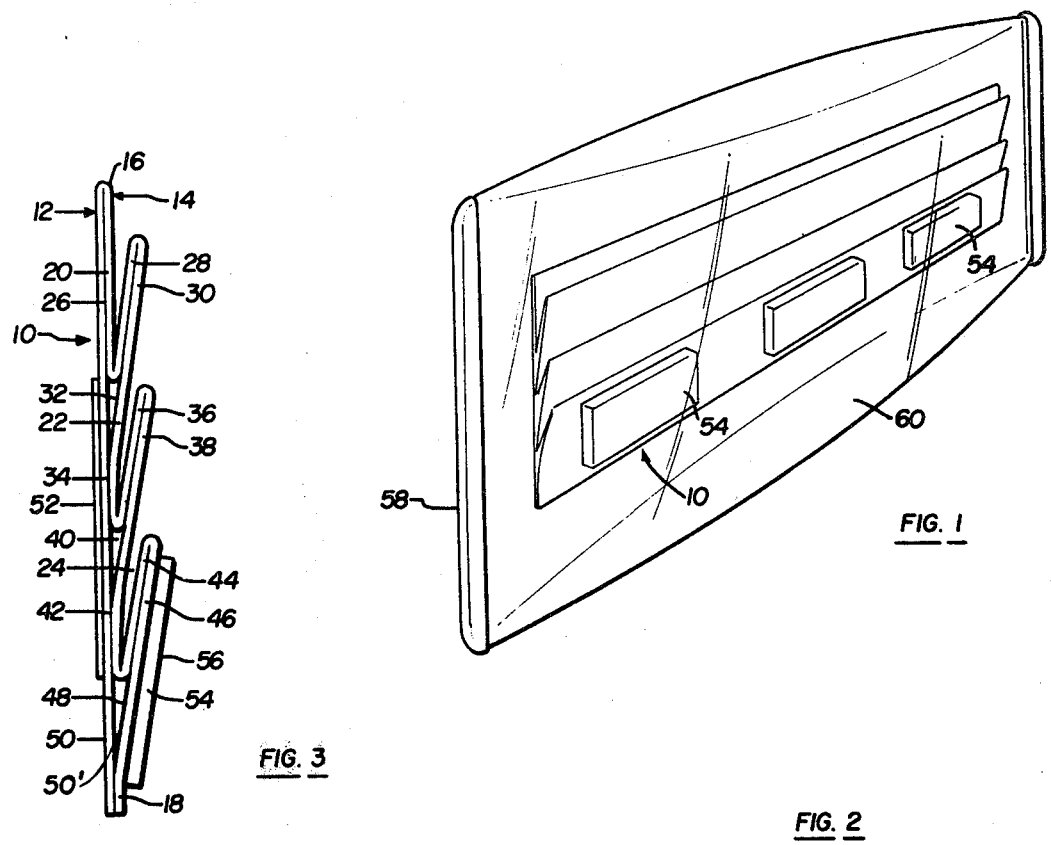
FIG. 1 is a perspective view of one embodiment of the holder and counter sealed in a transparent envelope.
FIG. 2 is a front view of the holder and counter shown shown in FIG. 1.
FIG. 3 is a side view of the holder and counter of FIG. 2.
Figure 4:
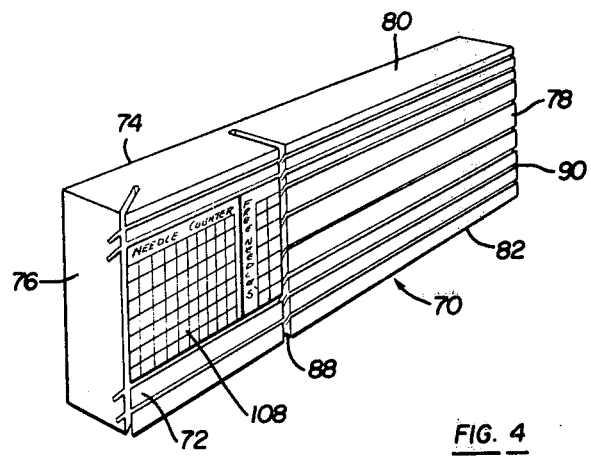
FIG. 4 is a perspective view of another embodiment of the holder and counter.

Referring now to FIGS. 1-3 inclusive, the holder and counter is designated by the numeral 10. It consists of a backing member 12 and a facing member 14, each made from a sheet of relatively thin yieldable or pliable material such as poster board, plastic or other sheet materials. The backing member 12 is elongated and is of rectangular cross section throughout its longitudinal extent as illustrated in FIG. 2 and also in transverse cross section as illustrated in FIG. 3.

The facing member 14 has upper and lower edge portions 16 and 18 which are adhesively secured to the opposing surface of the backing member 12 throughout their longitudinal extent. The facing member 14 prior to formation is of rectangular configuration, has a length equal to the length of the backing member 12 and has a width substantially greater than the width of the backing member 12 so that intermediate portions thereof may be bent and folded over other adjacent portions to form a plurality of pockets 20, 22 and 24 of V-shaped configuration as best illustrated in FIG. 3.

The first pocket 20 is formed by the longitudinal intermediate portion 26 which is adhesively secured to the backing sheet 12 throughout the longitudinal extent thereof and by the longitudinal intermediate portions 28 and 30 which are folded and adhesively secured together throughout the longitudinal extent thereof.

The second pocket 22 is formed by a longitudinal intermediate portion 32 which has the lower portion thereof secured to the backing sheet 12 at an area represented by the numeral 34 and by the reversely bent longitudinal intermediate portions 36, 38 of the facing sheet 14 which are secured together by a suitable adhesive. Finally, the third pocket 24 is formed by the longitudinal intermediate portion 40 having the lower edge thereof secured to the backing sheet 12 at an area represented by the numeral 42 and by the reversely bent longitudinal intermediate portions 44 and 46 which are adhesively secured together. Finally, the facing sheet 14 is provided with a longitudinal intermediate portion 48 terminating in the lower edge portion 18 which is adhesively secured to the facing sheet 12.

The portions 28 and 30, 36 and 38, and 44 and 46 extend upwardly and outwardly from the backing member 12 and form flexible arms which firmly hold the surgical packages in the V-shaped pockets.

The back side or surface 50 of the backing sheet 12 is provided with an elongated pressure-sensitive strip 52 which is centrally located thereon and extends substantially the entire length thereof. The front side or surface of the backing sheet is indicated by 50'. When in use, the backing strip 52 is removed to leave or to expose a pressure-sensitive adhesive surface so that the holder 10 can be applied to a support when in use such as a Mayo stand, back table or the like used in an operating room.

It should be appreciated that the backing and facing members 12 and 14 may be made from a single sheet of material which is cut, bent, folded and pleated to form the rack or holder 10. Although poster board of approximately 1/32" in thickness is now utilized as the material for holder 10, it should be appreciated that other pliable materials may be used such as cardboard, plastic and the like which are available in sheets or rolls.

The V-shaped pockets 20, 22 and 24 of the rack or holder 10 each has a uniform depth which is less than the depth of the packages inserted therein containing the needles and sutures. The pockets are filled or loaded with surgical products such as pre-packed sutured needles, reeled sutures, loose sutures 53 or ties, loose needles, etc. all of which are in a sterilized condition. The packages of sutures, needles, etc. are held firmly and conveniently in the pockets by the corresponding portions of the facing sheet 14. A surgeon viewing the loaded holder 10 can readily see the packages and the indicia thereon which permits ready identification of the size and type of sutures or suture-needle combinations. One package P is shown by dotted lines in FIG. 2. A plurality of packages are contained in each pocket.

The holder 10 is provided with one or more removable rectangular blocks 54 made from resilient material such as corrugated cardboard or polyfoam material which has on the outer or front surface thereof suitable indicia 56 which is used by the scrub nurse in rapidly counting the used needles. The indicia 56 is printed directly on the blocks 54 although decals could be applied to the blocks upon which the indicia is printed. The blocks are adhesively secured to the longitudinal intermediate portions 46 and 48 of facing member 14 midway between the side edges thereof. The blocks 54 can each be used to hold ten needles, one needle in each box numbered 1 to 10 inclusive.

As shown in FIG. 2, each block 54 has a heading or legend entitled "Needle Counter". Below the "Needle Counter" heading are a pair of horizontal rows of consecutive numbers, as an example, from 1 to 10 inclusive. Rows of blank boxes may also be provided where loose needles are to be used, one needle in a box. The blocks 54 are secured to the holder 10, under sterile conditions, and the assembly is inserted in the envelope 58 having at least one transparent face 60 which permits viewing of the holder 10 without opening the envelope 58. After packaging has been completed, the sealed envelope 58 including the blocks 54 thereon is then stored ready for use.

When in use, the holder 10 and blocks 54 are removed from the envelope 58 and the pockets are filled or loaded with surgical products under sterile condition such as pre-packaged sutured needles, reeled sutures, etc. as described previously.

After use, the needles are inserted into the numbered spaces on the block(s) 54. After each block 54 is filled with used needles, it is removed from the holder 10, exposing a protected adhesive strip, not shown, attached to the block 54. The backing strip on the adhesive strip is removed and the block 54 with the contaminated used needles is applied to some handy surface such as a counter top, back table or the like in the operating room.

Referring now to FIGS. 4-8 inclusive, the suture holder is designated by the numeral 70 and is fabricated from a generally rectangular shaped elongated block of polyfoam material which is an open cell porous polyethylene foam. The holder 70 has a top wall 72, bottom wall 74, end wall 76, end wall 78, side wall 80 and side wall 82.

Figure 8:
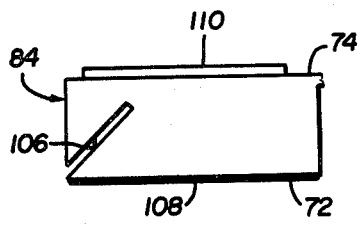
FIG. 8 is a side view of one section of the holder and counter of FIG. 5, after the other section of the device has been severed therefrom.
Figure 7:
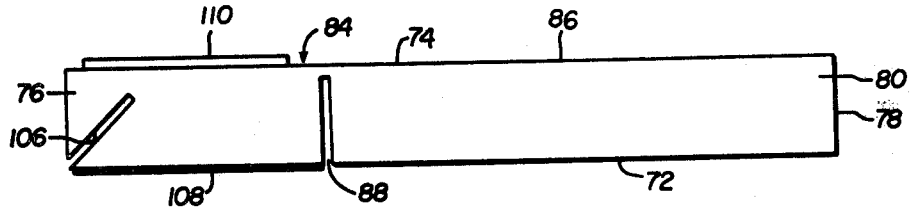
FIG. 7 is a side view of the holder and counter shown in FIG. 5.
Figure 5:
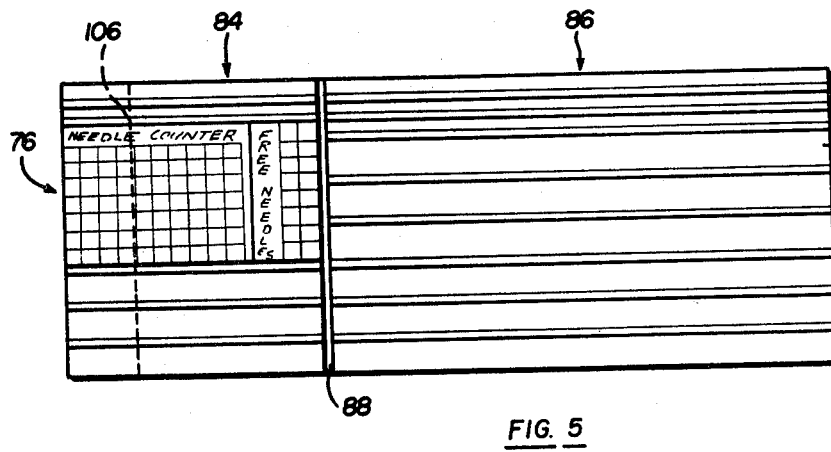
FIG. 5 is a top view of the holder and counter shown in FIG. 4.

The block is divided into two sections 84 and 86 which are separated by a laterally extending groove 88 which extends from the top wall 72 substantially through the block and terminating short of the bottom wall 74. It is sufficient to say at this time after the rack-holder 70 has been utilized and the used needles inserted into the holder 10 that a force may be applied to the bottom wall 74 of the holder 70 adjacent the groove 88 so as to divide or separate the block into the two sections 84 and 86. FIG. 8 shows section 84 after the other section 86 containing the used needles etc. has been discarded.

The block is provided with a plurality of saw kerfs or slots 90 which extend through the top wall 72 for a distance of about one inch towards the bottom wall 74 and at a 45° angle with respect to the top wall 72. The slots 90 extend longitudinally from end wall 78 to the groove 88 although such slots 90 may extend completely across the block from end wall 78 to end wall 76. Each slot 90 has side surfaces 92 and 94 and a bottom surface 96. The side surfaces 92 and 94 are uniformly spaced apart, as an example, 1/32". Surgical packages of sutures and needles are placed in the slots 90 and are held firmly therein. The packages contact the bottom surface 96 of slots 90 as well as the side surfaces 92, 94 and extend outwardly beyond the block's top wall 72 to permit a person to readily identify the size and type of suture or suture-needle combinations printed on the packages. Several packages P are shown in dotted lines in the slots 90 in FIG. 6. The packages P engage the side and bottom surfaces of slots 90 and are held firmly in place. The slots 90 are constructed to hold pre-packed sutured needles and reeled sutures.

Figure 6:
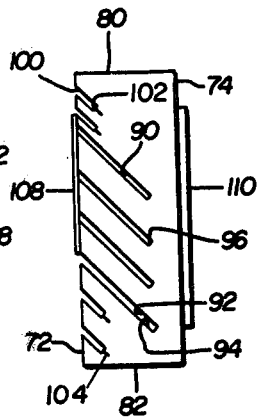
FIG. 6 is an end view of the holder and counter of FIG. 5.

The block is also provided with two additional pairs of saw kerfs or slots 100 arranged on opposite longitudinal sides of the slots 90 and parallel thereto as shown in FIG. 6. The slots 100 are at 45° with respect to the top wall 72 and extend therefrom a depth of only ¼". The slots 100 extend longitudinally from end wall 78 to end wall 76. The bottom surfaces 102 of the slots 100 are provided with knife slits 104 which extend a depth of ⅛". The knife slits 104 are for the purpose of holding loose or free sutures or ties, with the associated slots 100 serving as an aid in locating the slits 104.

The holder 70 is also provided with an angled slot 106 in the end wall 76 which is adapted to hold the needle holders when the operating room personnel are not using them.

The holder 70 is provided with a suitable paper decal 108 which has indicia thereon which is used by the scrub nurse in rapidly counting the used needles. The decal 108 is adhesively secured to the top wall 72 of the section 84 between the slots 100 provided therein. The decal 108 has two headings entitled "Needle Counter" and "Free Needles". Under the heading entitled "Needle Counter" there are a plurality of horizontal rows of consecutive numbers, as an example, from 1 to 70. That section aids the nurse in her final needle count by grouping the used needles into, as an example, groups of ten. Rows of blank boxes are provided for the "Free Needles" heading where the loose needles are carried or held.

The open cell porous polyethylene foam block or holder 70 may be placed in a sealed package, not shown and pre-sterilized by gamma radiation or by other sterilizing techniques. The holder is then stored for subsequent use.

The bottom wall 74 of section 84 is provided with a generally rectangular pressure-sensitive strip 110. The strip 110 when removed leaves or exposes a pressure-sensitive adhesive surface so that the holder 70 can be applied to a support such as a Mayo stand, back table or the like used in an operating room.

After use, the used needles are placed in section 86 and all the needles have been accounted for, the sections are separated by applying a force to wall 74 at the bottom of groove 88. Prior to separating, the scrub nurse rapidly counts the used needles by simply scanning the indicia. The scrub nurse must account for all the needles provided at the beginning of he operation. The marked decal section 84 is retained and the other section 86 provided with the used needles is thrown away.

The racks or holders 10 and 70 are designed to hold pre-threaded, pre-sterilized, pre-wrapped needle-suture combinations, suture reels (sutures wound on thin plastic reels), for ties (sutures intended for use without needles), and for free needles (unthreaded needles which will be threaded from the reels during surgery). In each embodiment, the pockets of holder 10 and the slots 90 of holder 70 hold the wrapped suture-needles in such a way to permit ready identification of the size and type. Such is achieved in holder 70 as a result of the angle (45°) and spacing of the slots 90.

Because of the large variety in types of operations and in techniques and peculiarities of surgeons, the holders may or may not be pre-loaded with packages of needles and sutures. Where the holders are not pre-loaded, they would be available in sterilized packages. In such case the scrub nurse would load the pre-sterilized block with the necessary sterilized sutures and needles immediately prior to surgery.

Referring now to FIGS. 9–15 inclusive, the holder and counter is designated by the numeral 120 and constitutes another embodiment of the present invention. It is similar to the holder and counter 10 of FIGS. 1–3 and in addition includes a foldable stand or easel for mounting the holder and counter 120 and for storing the needle holders as will subsequently appear.

The holder and counter 120 consists of a foldable or expandable backing member 122 and a facing member 124, each made from a sheet of relatively thin yieldable or pliable material such as poster board, plastic or other sheet materials.

The backing member 122 is elongated and of tubular construction as shown in FIG. 10 and forms the foldable easel or stand 126. The backing member 122 includes a plurality of foldable sections including a generally flat base section 128, a top section 130 having a fold line 132 and a mounting section 134 which is hingedly connected to base section 128 at a fold area or line 136 and to the top section 130 at a fold area or line 138. The top section 130 includes a pair of finger openings 140 to assist in the opening of the easel 126.

The facing member 124 has upper and lower edge portions 142 and 144 which are adhesively secured to the opposing surface of the base section 128 throughout their longitudinal extent. The facing member 124 prior to formation is of generally rectangular configuration and has a sufficient width so that intermediate portions thereof may be bent and folded over other adjacent intermediate portions to form a plurality of pockets 146, 148 and 150 of generally V-shaped configuration as best illustrated in FIG. 14.

The first pocket 146 is formed by the longitudinal intermediate portion 152 which is adhesively secured to the base section 128 throughout the longitudinal extent thereof and by the longitudinal intermediate portions 154 and 156 which are folded and adhesively secured together throughout the longitudinal extent thereof.

The second pocket 148 is formed by a longitudinal intermediate portion 158 which has the lower portion thereof secured by the base section 128 at an area represented by the numeral 160 and by the reversely bent longitudinal intermediate portions 162, 164 of the facing sheet 124 which are secured together by a suitable adhesive. Finally, the third pocket 150 is formed by the longitudinal intermediate portion 166 having the lower edge thereof secured to the base section 128 at an area represented by the numeral 168 and by the reversely bent longitudinal intermediate portions 170 and 172 which are adhesively secured together. Finally, the facing sheet 124 is provided with the longitudinal intermediate portion 174 terminating in the lower edge portion 144 which is adhesively secured to the facing sheet 124.

The portions 154 and 156, 162 and 164, and 170 and 172 extend upwardly and outwardly from the base section 128 and form flexible arms which firmly hold the surgical packages in the V-shaped pockets aforesaid.

The back side or surface 176 of the mounting section 134 of the backing member 122 is provided with an elongated pressure-sensitive strip 178 which is centrally located thereon and extends substantially the entire length thereof as shown in FIG. 13. When in use, the backing strip 178 is removed to leave or to expose a pressure-sensitive adhesive surface so that the holder 120 can be applied to a support when in use such as a Mayo stand, back table or the like used in an operating room. The holder 120 can be applied to a support at any inclination with the easel or stand 126 folded closed as in FIG. 14 or in an extended position as in FIG. 10.

It should be appreciated that the backing and facing members 122 and 124 may each be made from a single sheet of material which is cut, bent, folded and pleated to form the rack or holder 120. Although poster board of approximately 1/32" in thickness is now utilized as the material for holder 120, it should be appreciated that other pliable materials may be used such as cardboard, plastic and the like which are available in sheets or rolls.

The V-shaped pockets 146, 148 and 150 of the rack or holder 120 each has a uniform depth which is less than the depth of the packages inserted therein containing the needles and sutures. The pockets are filled or loaded with surgical products such as pre-packed sutured needles, reeled sutures, loose sutures 53 or ties, loose needles, etc. all of which are in a sterilized condition. The packages of sutures, needles, etc. are held firmly and conveniently in the pockets by the corresponding portions of the facing sheet 124. A surgeon viewing the loaded holder 120 can readily see the packages and the indicia thereon which permits ready identification of the size and type of sutures or suture-needle combinations as explained previously in connection with FIGS. 1–3. A plurality of packages are contained in each pocket as shown in the embodiment of FIG. 3.

The holder 120 is provided with one or more removable rectangular blocks 180 made from resilient material such as polyfoam material which has on the outer surface thereof suitable indicia 182 which is used by the scrub nurse in rapidly counting the used needles. The indicia 182 is printed directly on the blocks 54 although decals could be applied to the blocks 180 upon which the indicia is printed. Each block 180 is adhesively and removably secured to the longitudinal intermediate portions 172 and 174 of facing member 124 between the side edges thereof. The blocks 180 can each be used to hold ten needles, one needle in each box numbered, as an example, 1 to 10 inclusive under the heading "Needle Counter" as shown in FIG. 15. Rows of blank boxes may also be provided where loose needles are to be used, one needle in a numbered box.

Each block 180 is provided on the back side thereof opposite the indicia 182 with a pair of pressure-sensitive adhesive layers or strips 184 and 186. The first or outer adhesive strip 184, which may cover and protect the entire second strip 186 or a part thereof, is removed to expose an adhesive surface which is used to secure the block 180 to the facing member 124 of holder 120 as shown in FIG. 9. The blocks 180 are secured to holder 120 under sterile conditions and the assembly is inserted in an envelope 188 having at least one transparent face 190. After packaging has been completed, the sealed envelope 188 including the contents therein is then stored ready for use.

When in use, the holder 120 and blocks 180 are removed from the envelope 188 and the pockets are filled or loaded with surgical products under sterile conditions as described in connection with the other embodiments.

After use, the needles are inserted in the numbered spaces on the blocks 180. After each block 180 is filled with used needles, it is removed from the holder 120 and the strip 186 is removed exposing another adhesive surface on the block 180. The filled block 180 is then applied to some handy surface or location during the remaining surgery.

Once the blocks 180 have been filled with the used needles and the surgery completed, the filled blocks 180 are inserted in the interior or opening of the foldable easel or stand 126 and thereafter the end tabs 194 (FIG. 12) provided on the top section 130 are folded down and suitable end flaps 196 provided on the base section 128 are folded over the ends of the opening and cooperate with the end tabs 194 to close the interior of the easel 126. The holder 120 containing the used needle blocks 180 forms a protective pouch which may be discarded. The holder 120 thus protects a person from injury should the person handle the holder 120 when in a trash can.

Figure 17:
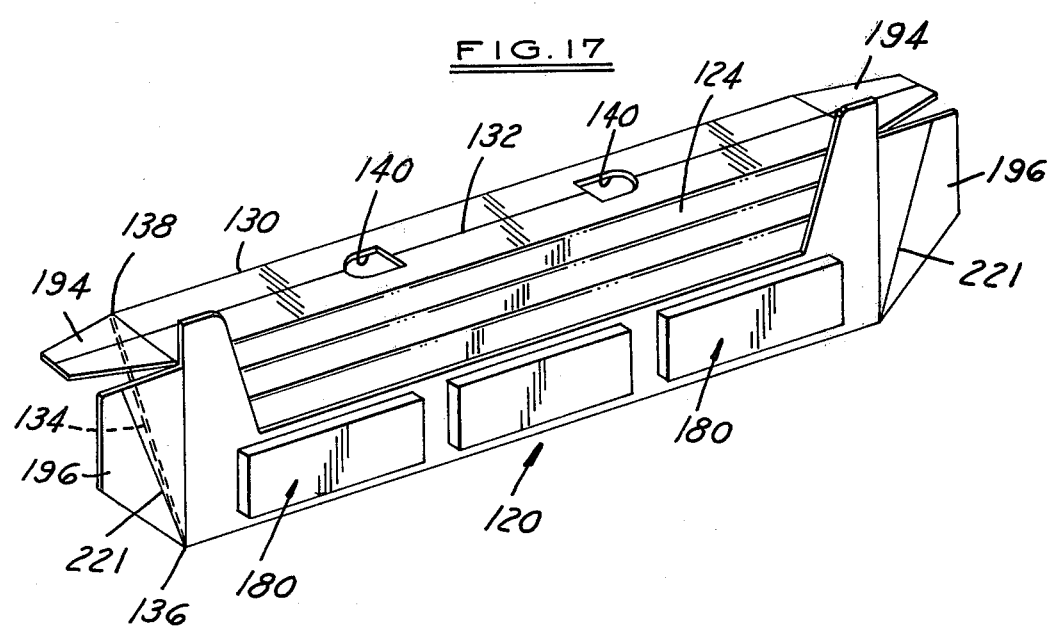
FIG. 17 is a perspective view of the holder and counter, with the package removed.

FIG. 17 is a perspective view of the holder and counter 120 with the envelope 188 removed. As clearly shown by FIG. 17, top section 130 has an end tab 194 on each end thereof. End flaps 196, attached to either base section 128 or mounting section 134, are folded over the ends of the opening formed when the holder 120 is expanded and after the end tabs 194 have been folded down. The fold line 221 for the end flaps 196 is shown in FIGS. 13 and 17.

With the present invention, the needle blocks are removable individually from the holder. Such blocks are also available in sealed sterile packages, with two or three blocks to a package. The individual blocks may be utilized for certain operations where more than thirty needles are required and thus will be available to supplement a holder having three needle blocks and a capacity of thirty needles.

The stand or easel 126 has several important functions including it provides support for the holder; makes it easier to view the contents of the holder; provides a place to store the needle holders during surgery within the interior of the stand; and provides a protected pouch into which the blocks containing the used needles may be dropped or placed for final disposal of contaminated material so as to minimize danger to janitorial personnel.

It should be appreciated that an actual numerical count of the needles is always necessary or required before surgery or that at least precautions be taken to retain the package labels which indicate the number of needles brought into the surgical room or field. The numbers on the block or blocks make it possible to obtain rapid accurate counts during and after surgery. The used needles are often counted several times during the surgery. The nurse need only scan the indicia which are stabbed by and retain the used needles and can quickly see where the needles are. The scanning permits the nurse to count the used needles in groups of ten, to glance at the last number containing a needle on the final or last block and the count is made. The prior art technique requires the nurse to lay the needles out one at a time and count them.

We claim:

1. A holder and counter for surgical products comprising a generally rectangular elongated block having a flat top wall, a flat bottom wall, opposing side walls and opposing end walls, a groove extending through the top wall and terminating short of the bottom wall and dividing said block into two sections, a decal with indicia thereon secured to said top wall of one of said sections, said other section having a plurality of parallel and lengthwise extending slots passing entirely through said top wall and extending towards said bottom wall, each slot having a pair of side surfaces which are spaced apart and a bottom surface, with each slot adapted to receive a surgical product, said first and second sections being severable by applying a force to the bottom wall adjacent said groove to separate said sections of the block.

2. The holder and counter defined in claim 1 wherein the surfaces of said slots are at a 45° angle with respect to said top wall.

3. The holder and counter defined in claim 1 wherein said block is made from polyfoam material.

4. The holder and counter defined in claim 1 wherein a pressure-sensitive adhesive strip is secured to said bottom wall for attaching the holder to a support.

* * * * *